United States Patent
Heath

(10) Patent No.: US 10,130,444 B1
(45) Date of Patent: Nov. 20, 2018

(54) ENDODONTIC INSTRUMENT

(71) Applicant: DENTSPLY SIRONA Inc., York, PA (US)

(72) Inventor: Derek Heath, Vero Beach, FL (US)

(73) Assignee: DENTSPLY SIRONA Inc., York, PA (US)

(*) Notice: Subject to any disclaimer, the term of this patent is extended or adjusted under 35 U.S.C. 154(b) by 0 days.

(21) Appl. No.: 15/650,045

(22) Filed: Jul. 14, 2017

(51) Int. Cl.
- *A61C 5/02* (2006.01)
- *A61C 5/42* (2017.01)
- *A61C 5/50* (2017.01)

(52) U.S. Cl.
CPC . *A61C 5/42* (2017.02); *A61C 5/50* (2017.02)

(58) Field of Classification Search
CPC .............. A61C 5/42; A61C 5/50; A61C 5/40
USPC ........................................ 433/81, 102, 224
See application file for complete search history.

(56) References Cited

U.S. PATENT DOCUMENTS

| | | | |
|---|---|---|---|
| 5,902,106 A * | 5/1999 | McSpadden | A61C 5/42 433/102 |
| 6,712,611 B2 * | 3/2004 | Garman | B24B 19/022 433/102 |
| 7,147,469 B2 * | 12/2006 | Garman | A61C 5/42 433/102 |
| 7,435,086 B2 | 10/2008 | Berutti et al. | |
| 7,662,170 B2 * | 2/2010 | Mashiko | A61B 17/06066 148/206 |
| 8,727,772 B2 | 5/2014 | Jaunberzins | |
| 2007/0031783 A1 * | 2/2007 | Cantatore | A61C 5/42 433/102 |
| 2007/0184406 A1 * | 8/2007 | Mason | B23B 51/0081 433/102 |
| 2010/0119990 A1 * | 5/2010 | Lampert | A61C 5/42 433/102 |
| 2010/0297578 A1 * | 11/2010 | Jaunberzins | A61C 5/42 433/102 |

* cited by examiner

*Primary Examiner* — Matthew Nelson
(74) *Attorney, Agent, or Firm* — Dentsply Sirona Inc.

(57) ABSTRACT

An endodontic instrument includes a plurality of flutes and a plurality of lands extending helically around a working portion. Each flute includes a curved concave flute surface, a pair of flute shoulders at the peripheral edges of the flute surface, a flute width defined by a distance between the flute shoulders, and a flute depth defined by a point of maximum depth between the flute shoulders. Each land is positioned between a pair of axially adjacent flutes and includes a curved concave land surface, a pair of land shoulders at the peripheral edges of the land surface, a land width defined by a distance between the land shoulders, and a land depth defined by a point of maximum depth between the land shoulders. The land width is less than the flute width and the land depth is less than the flute depth in the upper region of the working portion.

11 Claims, 4 Drawing Sheets

ENDODONTIC INSTRUMENT

FIELD

This disclosure relates to the field of endodontics. More particularly, this disclosure relates to instruments used for enlarging and obturating an extirpated root canal.

BACKGROUND

In the field of endodontics, one of the most important and delicate procedures is that of cleaning or extirpating a diseased root canal to provide a properly dimensioned cavity while essentially maintaining the central axis of the canal for filling of the canal void and capping of the tooth. When done properly, this step enables substantially complete filling of the canal with biologically inert or restorative material without entrapping noxious tissue in the canal that could lead to failure of the therapy.

In a root canal procedure, the dentist removes diseased tissue and debris from the canal prior to filling the canal with a biologically inert or restorative filling material. Many tools and techniques have been designed in an effort to enable dentists to perform the difficult task of cleaning and shaping root canals. Historically, dentists have used endodontic files to remove the soft and hard tissues in and adjacent the root canal. These endodontic files are typically made by grinding helical flutes into a working portion of a small elongate tapered rod to create a curvilinear, abrasive file with a helical cutting edge.

Conventional endodontic instruments with helical cutting/abrading edges have certain endemic problems which, to some degree, have been tolerated and approached from a management perspective rather than an elimination perspective. For example, conventional endodontic instruments may only cut when rotated in one direction. Further, the instruments typically must be backed off after rotating in a first direction to unload the instrument before advancing the instrument further into the root canal. Conventional endodontic instruments also may begin to screw into the wall of the canal rather than continuing down the canal toward the apical tip of the root. In some cases, this "screwing in" can cause the instrument to break through the side of the root canal and into surrounding tissue or bone. Or, it may begin to "drift" or displace laterally relative to the center axis of the canal as it is moved roto-axially.

These and other problems continue to plague practitioners and designers alike in their efforts to enlarge and prepare for filling the varied tooth root canal configurations in a manner substantially concentric with the natural or original canal curvature/shape to enable successful, effective and permanent treatment therapies. Accordingly, there is a need for improved endodontic instrument designs and methods that will avoid, minimize or eliminate drawbacks and problems associated with conventional endodontic instruments including, but not limited to, "screwing in" issues and the inability to cut in more than one direction encountered during the use of conventional endodontic instruments.

SUMMARY

The above and other needs are met by an endodontic instrument adapted to be axially reciprocated within a root canal to remove material from walls of the root canal having an elongate rod having a proximate end and an opposite distal tip end defining a working portion disposed between the proximate end and the distal tip end, the working portion including an upper region and a lower region; a plurality of flutes extending helically around the working portion, each flute including a curved concave flute surface, a pair of flute shoulders at the peripheral edges of the concave flute surface, a flute width defined by a distance between the pair of flute shoulders, and a flute depth defined by a point of maximum depth between the pair of flute shoulders; and a plurality of lands extending helically around the working portion, each land positioned between a pair of axially adjacent flutes and including a curved concave land surface, a pair of land shoulders at the peripheral edges of the concave land surface, a land width defined by a distance between the pair of land shoulders, and a land depth defined by a point of maximum depth between the pair of land shoulders. The land width is less than the flute width and the land depth is less than the flute depth in the upper region of the working portion.

According to certain embodiments, the land width is substantially the same as the flute width and the land depth is substantially the same as the flute depth in the lower region of the working portion. In certain embodiments, the land width is approximately ½ to ¾ of the flute width in the upper region of the working portion and/or the land depth is approximately ¼ to ½ of the flute depth in the upper region of the working portion.

According to certain embodiments, the plurality of flutes consists of three flutes and the plurality of lands consists of three lands.

According to certain embodiments, the flute and land shoulders form six distinct cutting edges, each of the six distinct cutting edges including a positive cutting angle of about 75° to about 110° and a negative cutting angle of about 5° to about 30° depending on whether the instrument is rotated in a clockwise or counterclockwise direction.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Figure 1:
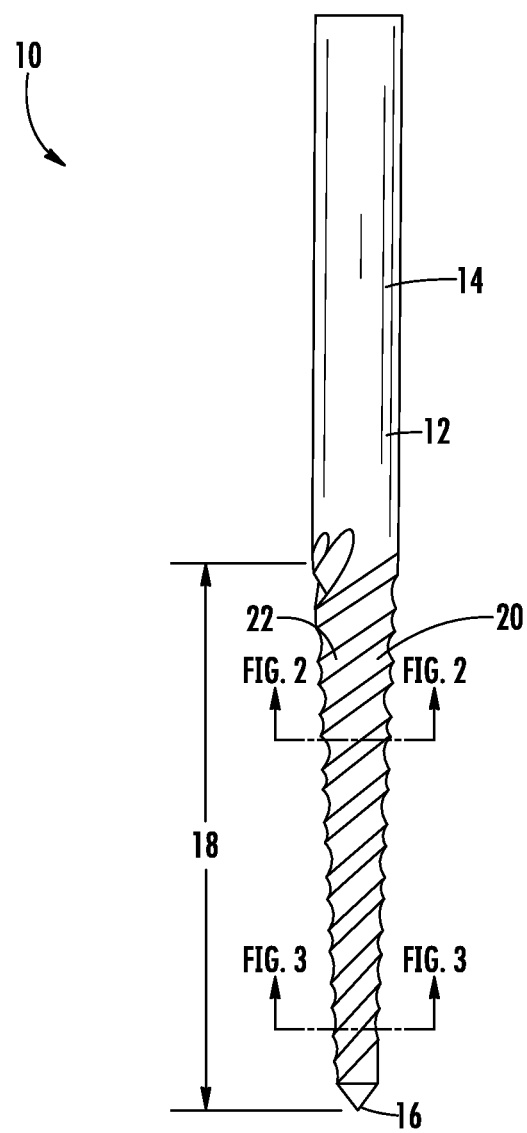
FIG. 1 shows a perspective view of an endodontic instrument according to one embodiment of the disclosure.
Figure 2:
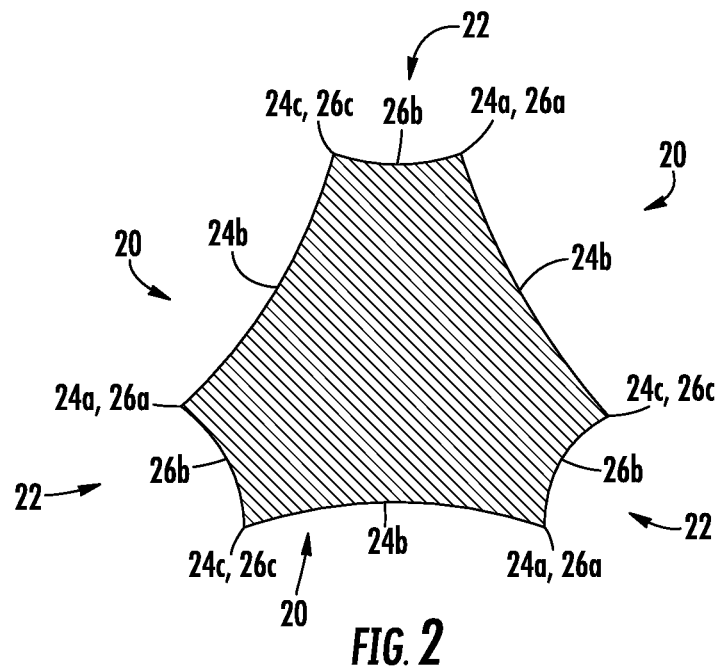
FIG. 2 shows a cross-sectional view of an endodontic instrument taken along lines A-A of FIG. 1 according to one embodiment of the disclosure.
Figure 3:
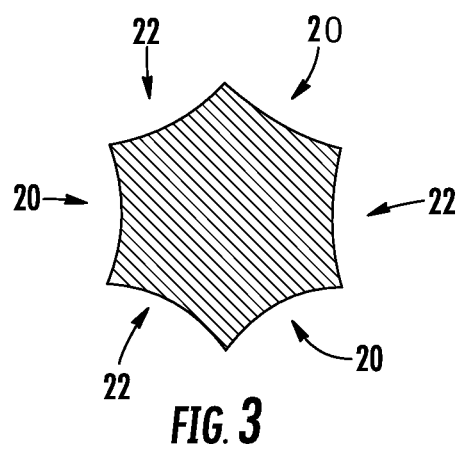
FIG. 3 shows a cross-sectional view of an endodontic instrument taken along lines B-B of FIG. 1 according to one embodiment of the disclosure.

FIGS. 1-3 illustrate features of an endodontic instrument 10 according to one embodiment of the present disclosure.

The elongate instrument is preferably formed from an elongate rod 12 of stainless steel or nickel-titanium alloy having a diameter of from about 0.3 millimeters to about 1.6 millimeters, although the rod 12 may have a larger or smaller diameter and/or a varying diameter along its length as needed. In suitable embodiments, rods 12 made from other suitable metals and/or alloys may be used. In one embodiment, the instrument 10 is formed from a controlled memory material allowing the instrument to be pre-formed before inserting the instrument into a root canal.

The elongate rod 12 extends from a proximal end 14 to a distal tip end 16 of the instrument 10. The proximal end 14 is typically secured to a fitting portion (not shown) for mating with a dental drill or hand-piece. In other embodiments, the proximal end 14 may be secured to a handle to facilitate hand manipulation of the instrument 10. The rod 12 includes a working portion 18 extending from adjacent the distal tip end 16 of the instrument 10 along the length of the rod 12 to adjacent the proximal end 14. The working portion 18 preferably has a length of from about 10 millimeters to about 20 millimeters. The diameter of the working portion 18 of the instrument 10 preferably tapers at a rate of from about 0.02 mm/mm to about 0.12 mm/mm, however it is also understood that the diameter of the working portion 18 may be substantially constant along a length of the working portion 18 and/or vary along a length of the working portion 18.

The working portion 18 of the instrument 10 includes two or more helical flutes 20 formed along a peripheral surface of the working portion 18. As best shown in FIG. 2, each of the flutes 20 define a curved concave flute surface when viewed in transverse cross section. Each flute 20 includes a pair of helical flute shoulders 24a and 24c at the peripheral edges of the concave flute surface. Each of the flutes 20 further include a flute base 24b defined by the point of maximum depth from the flute shoulders 24a and 24c. The peripheral surface of the working portion 18 of the instrument 10 further includes two or more helical lands 22 each positioned between axially adjacent flutes 20. Similar to flutes 20, each helical land 22 includes a curved concave land surface with helical land shoulders 26a and 26c at the peripheral edges of the concave land surface. As shown, each land shoulder 26a coincides with one of the flute shoulders 24a and each land shoulder 26c coincides with one of the flute shoulders 24c. Each of the lands 22 include a land base 26b defined by the point of maximum depth between land shoulders 26a and 26c. According to preferred embodiments, the instrument 10 preferably includes three helical flutes 20 formed along the working portion 18 of the instrument 10 and three helical lands 22 disposed between axially adjacent flutes 20. In alternate embodiments, the flutes and lands are straight as opposed to helical.

Referring to FIG. 2, which depicts the cross section of the working portion 18 of instrument 10 taken along line A-A of FIG. 1, the dimensions of the flutes 20 are preferably greater than the dimensions of the lands 22 in at least the upper region of the working portion 18 adjacent the proximal end 14. In particular, the width of the helical lands 22 are preferably smaller than the width of the flutes 20 and the land depth 26b is less than the flute depth 24b. According to preferred embodiments, the width of the lands 22 are approximately one-half to approximately three-quarters of the width of the flutes 20 in the upper region, and most preferably approximately two-thirds of the width of the flutes 20. According to preferred embodiments, the land depth 26b is approximately one-quarter to approximately one-half the flute depth 24b, and most preferably about one-third the flute depth 24b. For purposes of the present disclosure, the upper region of working portion 18 generally refers to the top portion adjacent the proximal end while the lower region generally refers to the lower portion adjacent the distal tip 16. In preferred embodiments, the upper region includes roughly the top two-thirds of the working portion 18 adjacent the proximal end 14 while the lower region of the working portion 18 includes roughly the lower third of the working portion 18 adjacent the distal tip 16.

Referring to FIG. 3, which depicts the cross section of the working portion 18 of instrument 10 taken along line B-B of FIG. 1, the dimensions of lands 22 are generally the same as the dimensions of the flutes 22 in the lower region of the working portion 18. As a result, according to preferred embodiments where the dimensions of the lands 22 are smaller than the dimensions of the flutes 20 in the upper region of the working portion 18 and generally the same in the lower region of the working portion 18, the flutes 20 and lands 22 of the lower region are configured to do more cutting of a canal cavity while the flutes and lands of the upper region are configured to transport debris out of the canal cavity. In preferred embodiments, the dimensions of lands 22 gradually conform to the dimensions of the flutes 22 as one moves from the upper region to the lower region of the working portion.

Figure 4A:
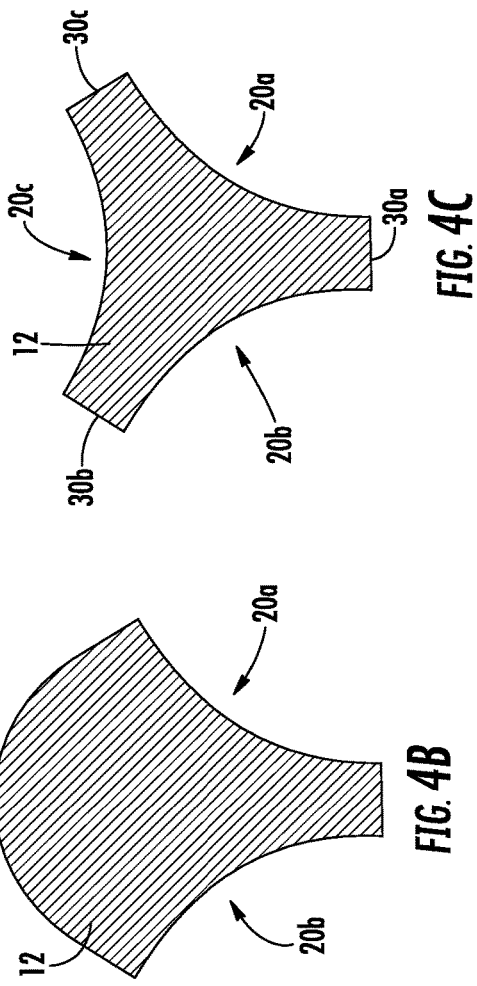
FIGS. 4A-4F illustrates a process for forming an endodontic instrument according to one embodiment of the disclosure using cross-sectional views of the upper region of a working portion of a rod following each pass of a rod past a grinding wheel.
Figure 4B:
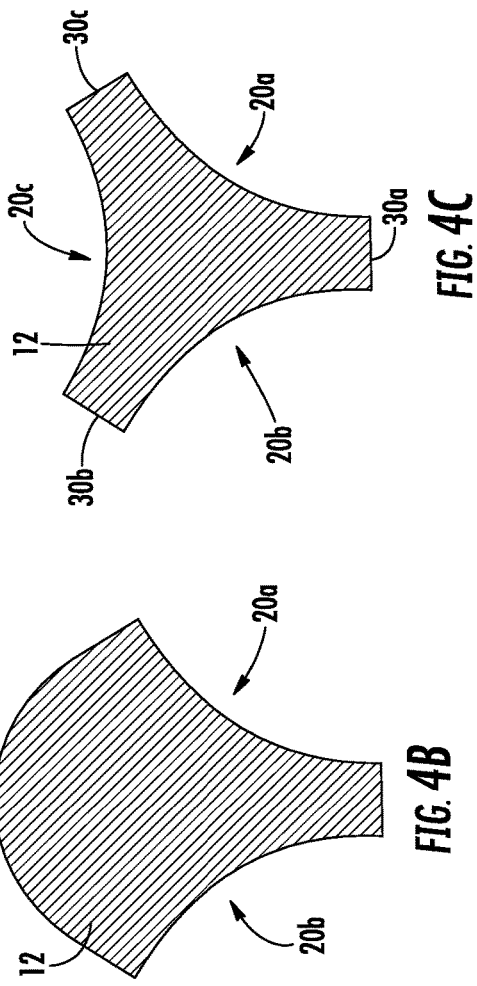
Figure 4C:
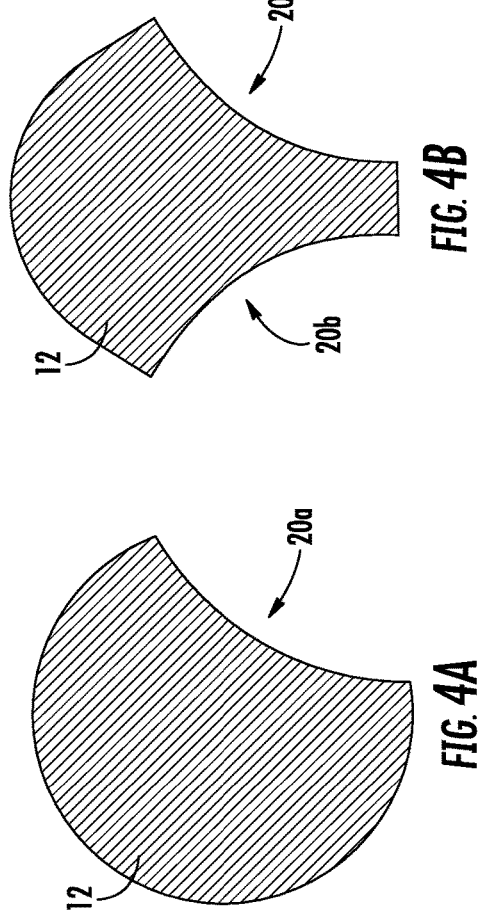

Referring to FIGS. 4A-4F, a process for grinding the flutes 20 and lands 22 of a three-fluted and three-land instrument 10 as shown in FIGS. 1-3 is depicted according to one embodiment of the disclosure. Referring to FIG. 4A, a rotating rod 12 is moved past a grinding wheel to form a first flute 20a in the rod 12. The rod 12 is then indexed and again moved past the grinding wheel a second time to form second flute 20b as shown in FIG. 4B, and indexed and moved past the grinding wheel a third time to form third flute 20c as shown in FIG. 4C. Referring to FIG. 4C, the cutting depths and widths of the flutes 20a, 20b, 20c are controlled to leave three convex outer surfaces 30a, 30b, 30c of the original rod 12 intact between axially adjacent flutes.

Figure 4D:
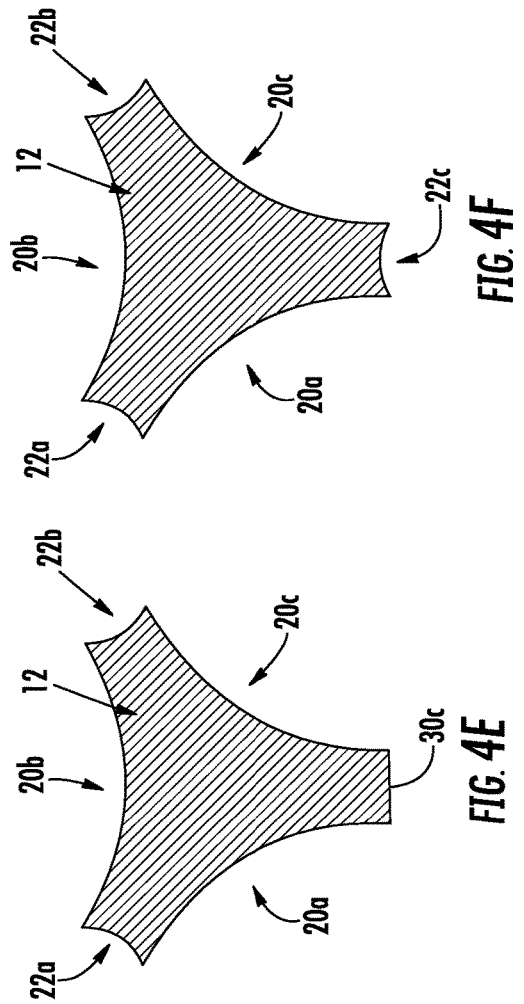
Figure 4E:
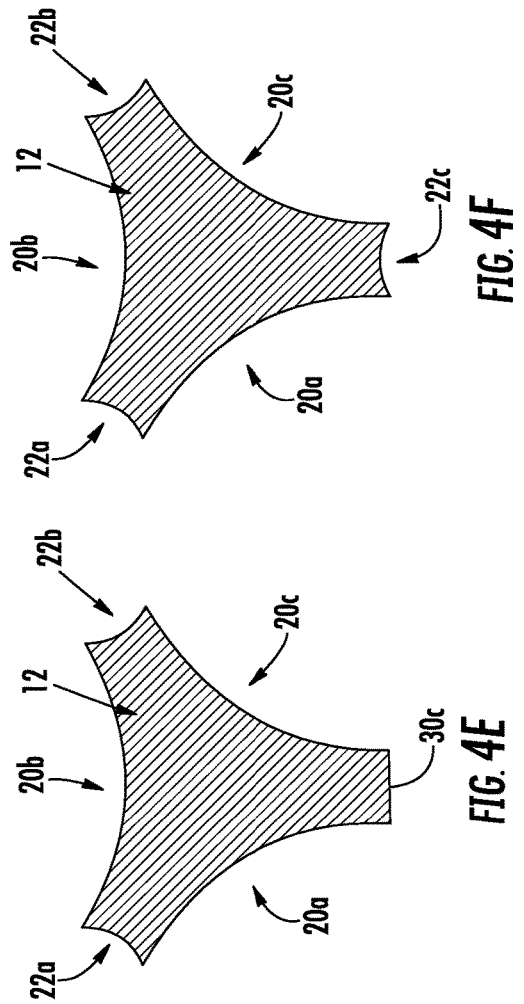
Figure 4F:
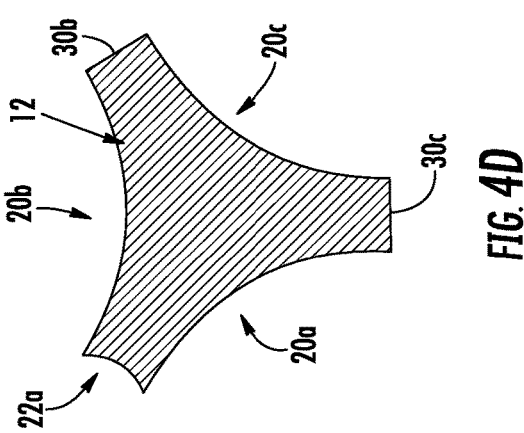

After forming the three flutes 20a, 20b, and 20c, rod 12 is indexed such that the rod's fourth pass past the grinding wheel begins between axially adjacent flutes 20a, 20b to form helical land 22a in convex outer surface 30a as shown in FIG. 4D. Rod 12 is again indexed and moved past the grinding wheel a fifth time to form helical land 22b in convex outer surface 30b as shown in FIG. 4E and a sixth time to form helical land 22c in convex outer surface 30c as shown in FIG. 4F.

As compared to traditional processes, the flutes 20 are cut into instrument 10 at a relatively shallow depth 20b using a smaller radius wheel to leave convex outer surfaces 30a, 30b, 30c with a sufficient width for forming lands 22. In preferred embodiments, the grinding wheel has a radius of about 0.01 inches to about 0.02 inches, and most preferably about 0.015 inches, resulting in a depth 20b of flutes in the upper region of working portion 18 of about 0.01 inches to about 0.02 inches, and most preferably about 0.015 inches. This compares to more traditional processes using a grinding wheel with a radius of about 0.01 inches to about 0.03 inches.

Figure 5:
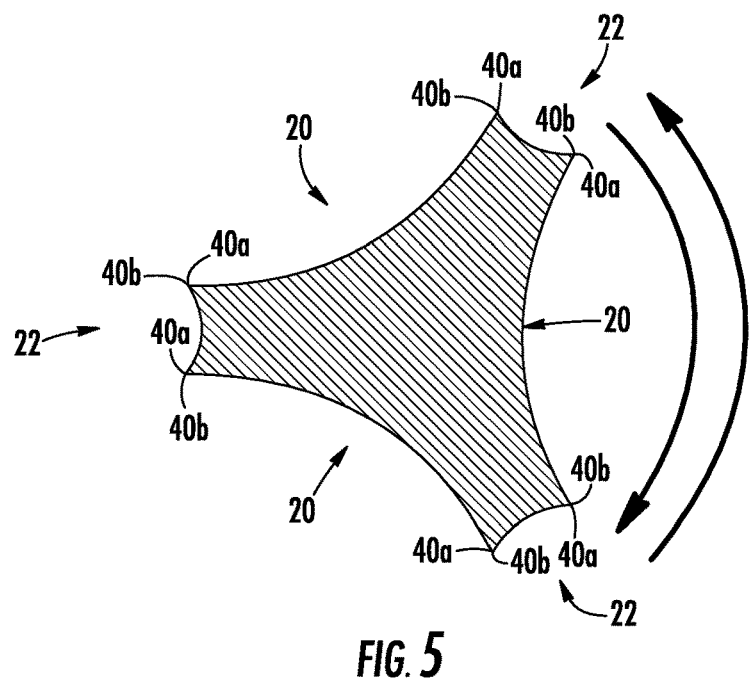
FIG. 5 shows a cross-sectional view of the cutting edges in the upper region of a working portion of an endodontic instrument according to one embodiment of the disclosure.
Figure 6:
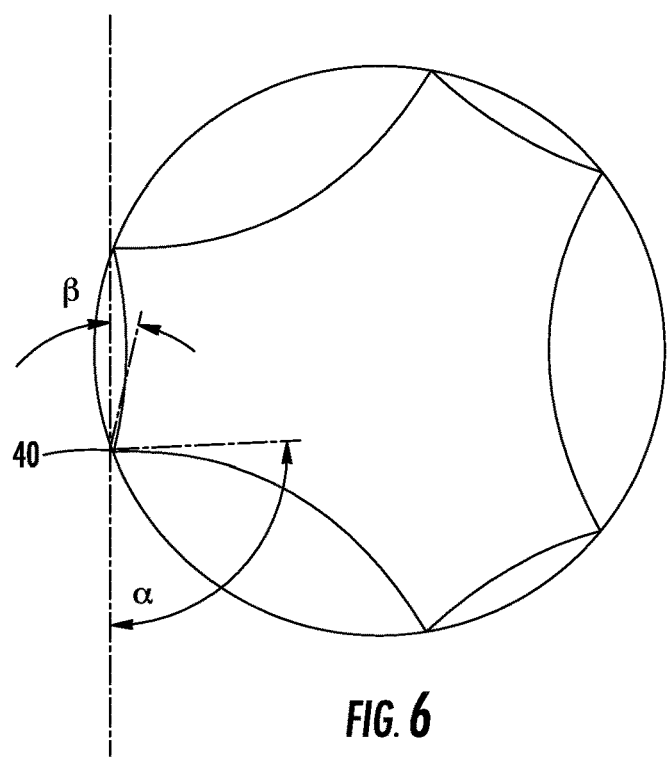
FIG. 6 illustrates the cutting angles of the cutting edges of FIG. 5 according to one embodiment of the disclosure.

Referring to FIG. 5, the six passes of rod 12 past the grinding wheel as described above forms an instrument with three concave flute surfaces 20 and three concave land surfaces 22 disposed between axially adjacent flutes 20. This results in the peripheral edges of the flutes 20 and lands 22 in the upper region of the working portion 18 forming six distinct cutting edges 40a when the instrument 10 is rotated in the clockwise direction and six distinct cutting edges 40b when the instrument 10 is rotated in the counterclockwise direction. More specifically, referring to cutting edge 40 depicted in FIG. 6, each cutting edge 40 in the upper region of the working portion includes either a positive cutting angle α of about 75° to about 110°, and most preferably about 95° about or a negative cutting angle β of about 5° to about 35°, and most preferably about 25° depending on which direction the instrument 10 is rotated due to the flutes 20 having a greater width and depth as compared to lands 22. In this regard, cutting edge 40 includes a positive cutting angle when the instrument 10 is rotated such that the cutting edge 40 trails flute 20 while cutting edge 40 includes a negative cutting angle when the instrument is rotated such that cutting edge 40 trails land 22. Accordingly, cutting edges 40a as shown in FIG. 5 includes three positive cutting edges and three negative cutting edges when rotated in the clockwise direction, and cutting edges 40b include three positive cutting edges and three negative cutting edges when rotated in the counterclockwise direction.

In use, the cutting edges with larger cutting angles make an aggressive and sharp cutting edge, which does the majority of cutting in the root canal. On the other hand, the negative cutting angles are less aggressive and will mostly clean and finish the cuts performed by the larger cutting angles. The negative cutting angles also provide a path for the micro cuts of debris to flow out of the root canal. Multi-directional cutting is also enhanced due to the positions of the positive and negative cutting angles in the instrument 10.

As noted above, the lower region of the working portion 18 preferably includes lands 22 with substantially the same width and depth as flutes 20. More specifically, referring back to FIG. 2, the lower region preferably includes six cutting edges 40 each having mostly negative cutting angles of about the same size whether the instrument is rotated in the clockwise or counterclockwise direction. Thus, the lower region of the working portion 18 preferably includes all sharp cutting edges.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. An endodontic instrument adapted to be axially reciprocated within a root canal to remove material from walls of the root canal, the endodontic instrument comprising:
    an elongate rod having a proximate end and an opposite distal tip end defining a working portion disposed between the proximate end and the distal tip end, the working portion including an upper region and a lower region;
    a plurality of flutes extending helically around the working portion, each flute including a curved concave flute surface, a pair of flute shoulders at the peripheral edges of the concave flute surface, a flute width defined by a distance between the pair of flute shoulders, and a flute depth defined by a point of maximum depth between the pair of flute shoulders; and
    a plurality of lands extending helically around the working portion, each land positioned between a pair of axially adjacent flutes and including a curved concave land surface, a pair of land shoulders at the peripheral edges of the concave land surface, a land width defined by a distance between the pair of land shoulders, and a land depth defined by a point of maximum depth between the pair of land shoulders,
    wherein the land width is less than the flute width and the land depth is less than the flute depth in the upper region of the working portion.

2. The endodontic instrument of claim 1 wherein the land width is substantially the same as the flute width and the land depth is substantially the same as the flute depth in the lower region of the working portion.

3. The endodontic instrument of claim 2 wherein the upper region of the working portion includes about two-thirds of the working portion and the lower region includes about one-third of the working portion.

4. The endodontic instrument of claim 1 wherein the land width is approximately ½ to ¾ of the flute width in the upper region of the working portion.

5. The endodontic instrument of claim 1 wherein the land width is approximately ⅔ of the flute width in the upper region of the working portion.

6. The endodontic instrument of claim 1 wherein the land depth is approximately ¼ to ½ of the flute depth in the upper region of the working portion.

7. The endodontic instrument of claim 1 wherein the land depth is approximately ⅓ of the flute depth in the upper region of the working portion.

8. The endodontic instrument of claim 1 wherein the land width is approximately ½ to ¾ of the flute width and the land depth is approximately ¼ to ½ of the flute depth in the upper region of the working portion.

9. The endodontic instrument of claim 1 wherein the land width is approximately ⅔ of the flute width and the land depth is approximately ⅓ of the flute depth in the upper region of the working portion.

10. The endodontic instrument of claim 1 wherein the plurality of flutes consists of three flutes and the plurality of lands consists of three lands.

11. The endodontic instrument of claim 1 wherein the flute and land shoulders form six distinct cutting edges, each of the six distinct cutting edges including a positive cutting angle of about 75° to about 110° and a negative cutting angle of about 5° to about 30° depending on whether the instrument is rotated in a clockwise or counterclockwise direction.

* * * * *